United States Patent
Ross et al.

(10) Patent No.: US 9,125,731 B2
(45) Date of Patent: Sep. 8, 2015

(54) ARTIFICIAL ANTERIOR CHAMBER SYSTEM

(75) Inventors: Rodney L. Ross, Mission Viejo, CA (US); James R. Dennewill, Laguna Hills, CA (US)

(73) Assignee: Med-Logics, Inc., Laguna Hills, CA (US)

(*) Notice: Subject to any disclaimer, the term of this patent is extended or adjusted under 35 U.S.C. 154(b) by 0 days.

(21) Appl. No.: 13/224,276

(22) Filed: Sep. 1, 2011

(65) Prior Publication Data
US 2012/0065655 A1 Mar. 15, 2012

Related U.S. Application Data

(63) Continuation-in-part of application No. 12/370,173, filed on Feb. 12, 2009, which is a continuation-in-part of application No. 11/366,043, filed on Mar. 1, 2006, now Pat. No. 8,070,764.

(51) Int. Cl.
*A61F 9/00* (2006.01)
*A61F 9/013* (2006.01)

(52) U.S. Cl.
CPC .................................. *A61F 9/0133* (2013.01)

(58) Field of Classification Search
CPC ....... A61F 9/0133; A61F 9/013; A61F 9/007; A61F 9/00754; A61F 2009/00872; A61F 2/14; A61F 2/142; A61F 2/145
USPC ......... 606/166, 107, 172, 169, 171, 180, 167, 606/4, 5, 170; 623/5.11, 6.12; 604/294, 22
See application file for complete search history.

(56) References Cited

U.S. PATENT DOCUMENTS

| | | | | |
|---|---|---|---|---|
| 4,865,033 A | * | 9/1989 | Krumeich et al. | 606/166 |
| 6,045,563 A | | 4/2000 | Duprat | |
| 6,425,905 B1 | * | 7/2002 | Guimaraes et al. | 606/166 |
| 6,622,729 B1 | * | 9/2003 | Peyman | 128/898 |
| 2006/0155261 A1 | * | 7/2006 | Bek et al. | 606/1 |
| 2008/0249548 A1 | | 10/2008 | Weston | |
| 2008/0269769 A1 | | 10/2008 | Dybbs | |
| 2011/0015512 A1 | | 1/2011 | Pan | |

\* cited by examiner

*Primary Examiner* — Jocelin Tanner
(74) *Attorney, Agent, or Firm* — David P. Gloekler

(57) ABSTRACT

A microkeratome cutting head includes a head structure, an applanation plate, and a stromal plate. The head structure may include a blade cavity for receiving a blade and a blade opening through which the blade extends. The blade is configured for creating a corneal flap at a corneal flap thickness. The applanation plate is disposed at an elevation above the stromal plate plane. The elevation difference is approximately equal to the corneal flap thickness. An artificial anterior chamber (AAC) system is used to hold the donor eye for interfacing with the microkeratome. The AAC system includes an optional pressure valve and pressure gauge in a closed loop system for the user or surgeon to control line pressure applied to the donor eye during the procedure.

4 Claims, 10 Drawing Sheets

US 9,125,731 B2

ARTIFICIAL ANTERIOR CHAMBER SYSTEM

CROSS-REFERENCE TO RELATED APPLICATIONS

This application is a continuation-in-part (CIP) of co-pending parent application Ser. No. 12/370,173, filed Feb. 12, 2009, which is a continuation-in-part (CIP) of application Ser. No. 11/366,043, filed Mar. 1, 2006, the contents of all of which are hereby incorporated by reference.

TECHNICAL FIELD

The present invention generally relates to procedures entailing the cutting of corneal tissue and to microkeratomes and related components utilized to cut corneal tissue. In particular, the present invention relates to cutting heads of microkeratomes that include non-coplanar applanation plates and stromal plates.

BACKGROUND

There have been developed a number of different surgical techniques to correct hyperopic or myopic conditions of a human eye. U.S. Pat. No. 4,840,175 issued to Peyman discloses a procedure wherein a thin layer of a cornea is cut to expose the stroma layer of the cornea. A laser beam is then directed onto the exposed corneal tissue in a predetermined pattern. The laser beam ablates corneal tissue and changes the curvature of the eye. This procedure is sometimes referred to as Laser in situ Keratomileusis (LASIK).

U.S. Pat. No. Re 35,421 issued to Ruiz et al. discloses a device for cutting a cornea in a LASIK procedure. Such a device is commonly referred to as a microkeratome. The Ruiz microkeratome includes a ring that is placed onto a cornea and a blade that is located within an opening of the ring. The device also contains a drive mechanism which moves the blade across the cornea in a first direction while the blade moves in a reciprocating transverse direction to cut the eye. The device can create a lamella flap of the cornea which is flipped back so that the stromal bed of the cornea can be ablated with a laser.

U.S. Pat. No. 6,051,009 issued to Hellenkamp et al. discloses a microkeratome that is sold under the trademark HANSATOME. The HANSATOME microkeratome moves the blade in an arcuate path about the cornea. The HANSATOME microkeratome includes a disposable blade assembly that can be loaded and removed from the device. The blade assembly includes a blade holder that is attached to a cutting blade. The blade holder has a recess that receives the end of a drive shaft. Rotation of the output shaft moves the blade in an arcuate path, and moves the blade in a back-and-forth motion to create the lamella flap of the cornea.

Microkeratomes have three primary components, a hand piece that contains a motor, a head that holds the blade, and a ring that applies a suction to maintain the position of the microkeratome relative to the cornea. Because the microkeratome is in contact with patient tissue it must be cleaned after each procedure, typically involving an autoclave. The head has a number of small cavities that are more difficult to clean. Additionally, the autoclave process may degrade the head after a number of procedures and cleaning cycles. It would be desirable to provide a microkeratome that does not require the head to be sterilized after each surgical procedure.

The blades used to cut tissue are replaced after each procedure. The replacement blades are typically loaded into the head of the microkeratome with a pair of forceps. The blade must be loaded accurately so that a drive pin of the motor assembly is inserted into a corresponding slot of a blade holder. Accurately loading the blade with forceps can be a time consuming process. It would be desirable to provide a blade package that can be used to accurately load a blade into a microkeratome in a time efficient manner.

A complication may occur while the microkeratome is cutting the lamella flap. It may be desirable to remove the microkeratome in the middle of a cut. Removing the microkeratome requires releasing the vacuum of the suction ring. Releasing the vacuum allows the cornea to move back to its original shape. Movement of the cornea will also cause the blade to move. Movement of the blade may cause damage to the cornea. It would be desirable to provide a microkeratome that allows a surgeon to remove the head while the suction ring is still fixed to the cornea. It would also be desirable to provide a microkeratome that allows the surgeon to vary the thickness of the lamella flap hinge.

Another problem attending the use of microkeratome cutting heads of known designs is the occurrence of a buttonhole (or dimple) in the cornea, which is a result of the cutting procedure. A buttonhole generally is a depression in the central region of the cornea, which results in an uncut island of tissue and is created as a conventionally designed cutting head passes over the cornea. The buttonhole is highly undesirable as it results in the blade cutting only the peripheral tissue that is at a higher elevation than the tissue in the central cornea where the buttonhole exists. Thus, a flap having a hole at its center is thereby created instead of an intended continuous or unbroken corneal flap. The occurrence of the buttonhole and consequent peripheral cutting event typically require that the surgeon lay the corneal flap (having the hole in its center) back down on the stromal bed of the cornea and wait a few months to attempt the intended procedure again. Therefore, there is also a need for providing a microkeratome that prevents the occurrence of such buttonholes, dimples, or depressions in the corneal tissue.

The microkeratome is commonly used in conjunction with an artificial anterior chamber (AAC) were the donor eye is situated, and creates a fixture from which the microkeratome can retrieve a graft. Examples of an artificial anterior chamber include U.S. Pat. No. 6,045,563 to Duprat; U.S. Patent Application Publication No. US2008/0249548 to Weston; and U.S. Patent Application Publication No. US2008/0269769 to Dybbs.

SUMMARY OF THE INVENTION

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one implementation, a microkeratome cutting head includes a head structure, an applanation plate, and a stromal plate. The head structure may include a front side, a back side, a bottom side between the front side and the back side, a top side, a blade cavity disposed in the head structure and configured for receiving a blade, and a blade opening disposed at the bottom side and through which the blade extends. The blade is configured for creating a corneal flap at a corneal flap thickness. The stromal plate may be disposed at the bottom side between the blade opening and the back side, and lies in a stromal plate plane. The applanation plate may be disposed at the bottom side between the blade opening and the front side. The applanation plate is disposed at an elevation above the stromal plate plane, relative to an axis perpendicular to the stromal plate plane and directed generally from the bottom side toward the top side. The elevation from the stromal plate plane to the applanation plate is approximately equal to the corneal flap thickness.

According to another implementation, a microkeratome includes a hand piece, a head coupled to the hand piece, and a blade. The head may include a front side, a back side, a bottom side between the front side and the back side, a top side, a blade cavity disposed in the head structure, a blade opening disposed at the bottom side, a stromal plate, and an applanation plate. The stromal plate is disposed at the bottom side between the blade opening and the back side, and lies in a stromal plate plane. The applanation plate is disposed at the bottom side between the blade opening and the front side. The blade may be disposed in the blade cavity and extend out from the bottom side through the blade opening. The blade is configured for creating a corneal flap at a corneal flap thickness. The applanation plate is disposed at an elevation above the stromal plate plane, relative to an axis perpendicular to the stromal plate plane and directed generally from the bottom side toward the top side. The elevation of the applanation plate relative to the stromal plate is approximately equal to the corneal flap thickness.

According to another implementation, a method is provided for creating a corneal flap in a cornea. A cutting head of a microkeratome is moved across the cornea. While moving the cutting head, the cornea is flattened by contacting the cornea with an applanation plate of the cutting head such that the applanation plate passes over the cornea. While the cornea is flattened, a corneal flap is created by contacting the cornea with a cutting edge of a blade extending out from the cutting head. While the cornea is being cut, a buttonhole is prevented from forming in the cornea by contacting the cornea with a stromal plate of the cutting head, the stromal plate being located behind the cutting edge relative to the applanation plate.

According to another implementation, a method is provided for fabricating a microkeratome cutting head. A head structure configured for coupling to a microkeratome hand piece is formed. A blade cavity and a blade opening are formed in the head structure. The blade cavity is configured for receiving a blade such that the blade extends through the blade opening and the blade is positioned for creating a corneal flap at a corneal flap thickness. An applanation plate is formed in front of the blade opening and at a bottom side of the head structure from which the blade extends, the applanation plate lying in an applanation plate plane. A stromal plate is formed behind the blade opening and at the bottom side, such that the stromal plate is positioned at an elevation below the applanation plate plane. The elevation difference between the applanation plate and the stromal plate is set to be approximately equal to the corneal flap thickness.

In an alternative embodiment, the present invention further contemplates an artificial anterior chamber system that interfaces the microkeratome. The system is intended for preparing stromal/endothelial cell tissue from a donor eye using the microkeratome, the system comprising an artificial anterior chamber (AAC) device having a housing; a chamber within the housing configured for receiving a donor eye and maintaining the donor eye at an applied pressure; an opening communicating with the chamber, the opening configured for exposing a corneal section of the donor eye and mounting the microkeratome in a position at which the microkeratome can interface with the donor eye; and a first fluid connector communicating with the chamber in a closed loop system; a fluid pressure source having a second fluid connector; a first fluid conduit connected between the AAC device and the fluid pressure source at the first fluid connector and the second fluid connector, respectively, and having a third fluid connector (e.g., a T connector) located along a length of the first fluid conduit; a second fluid conduit connected to the third fluid connector; and a pressure monitoring gauge of the closed loop system having a fourth fluid connector connected to the second fluid conduit, and a display configured for displaying an indication of the pressure applied by the fluid pressure source to the chamber.

The present invention further contemplates a method for preparing stromal/endothelial cell tissue of a donor eye for endothelial keroplasty using a microkeratome having a cutting head, the method comprising mounting the donor eye in a chamber of an artificial anterior chamber (AAC) device such that a corneal section of the donor eye is exposed via an opening of the AAC device; mounting the microkeratome in the opening such that the corneal section is accessible by the cutting head of the microkeratome; placing a fluid pressure source in communication with the chamber in a closed loop system by interconnecting a first fluid conduit between the fluid pressure source and the chamber; placing a pressure monitoring gauge in communication with the chamber by interconnecting a second fluid conduit between the pressure monitoring gauge and the first fluid conduit, at a location of the first fluid conduit between the fluid pressure source and the AAC device; applying pressure to the donor eye by operating a fluid pressure source communicating with the chamber via a first fluid conduit; cutting stromal/endothelial cell tissue from the donor eye by operating the microkeratome; while cutting, monitoring the pressure applied to the donor eye by operating the pressure monitoring gauge in the closed loop system, wherein the pressure monitoring gauge displays an indication of the pressure being applied; and based on the pressure indication displayed, adjusting the fluid pressure source to maintain the applied pressure within a range of about 75 to 125 mmHg.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION OF THE PREFERRED EMBODIMENTS

Disclosed is a microkeratome that includes a latch assembly that couples a head to a hand piece. The latch assembly allows the head to be readily detached from the hand piece and sterilized. There is no need to also sterilize the hand piece. The microkeratome also has a ring assembly that is coupled to the head and the hand piece. The ring assembly may include a fastener that can be unfastened to allow the hand piece and head to be detached from the ring, even while the ring assembly is fixed to a cornea.

The hand piece includes a motor that moves the blade across the ring. The microkeratome may have an aspiration connector with a collar that limits the travel of the blade and the thickness of a resulting lamella flap. The aspiration connector can be replaced with a collar of a different diameter to produce a flap with a different thickness. This allows a surgeon to select a flap hinge thickness.

The blade may be loaded into the microkeratome with a blade shuttle. The blade shuttle may have a plunger that pushes the blade into the microkeratome head. The movement of the plunger may be limited by a stop within the shuttle. The stop assists in accurately locating the blade within the head.

Also disclosed is a microkeratome head that includes an applanation plate and a stromal plate disposed in a non-coplanar configuration in which the stromal plate is at a lower elevation than the applanation plate.

Figure 1:
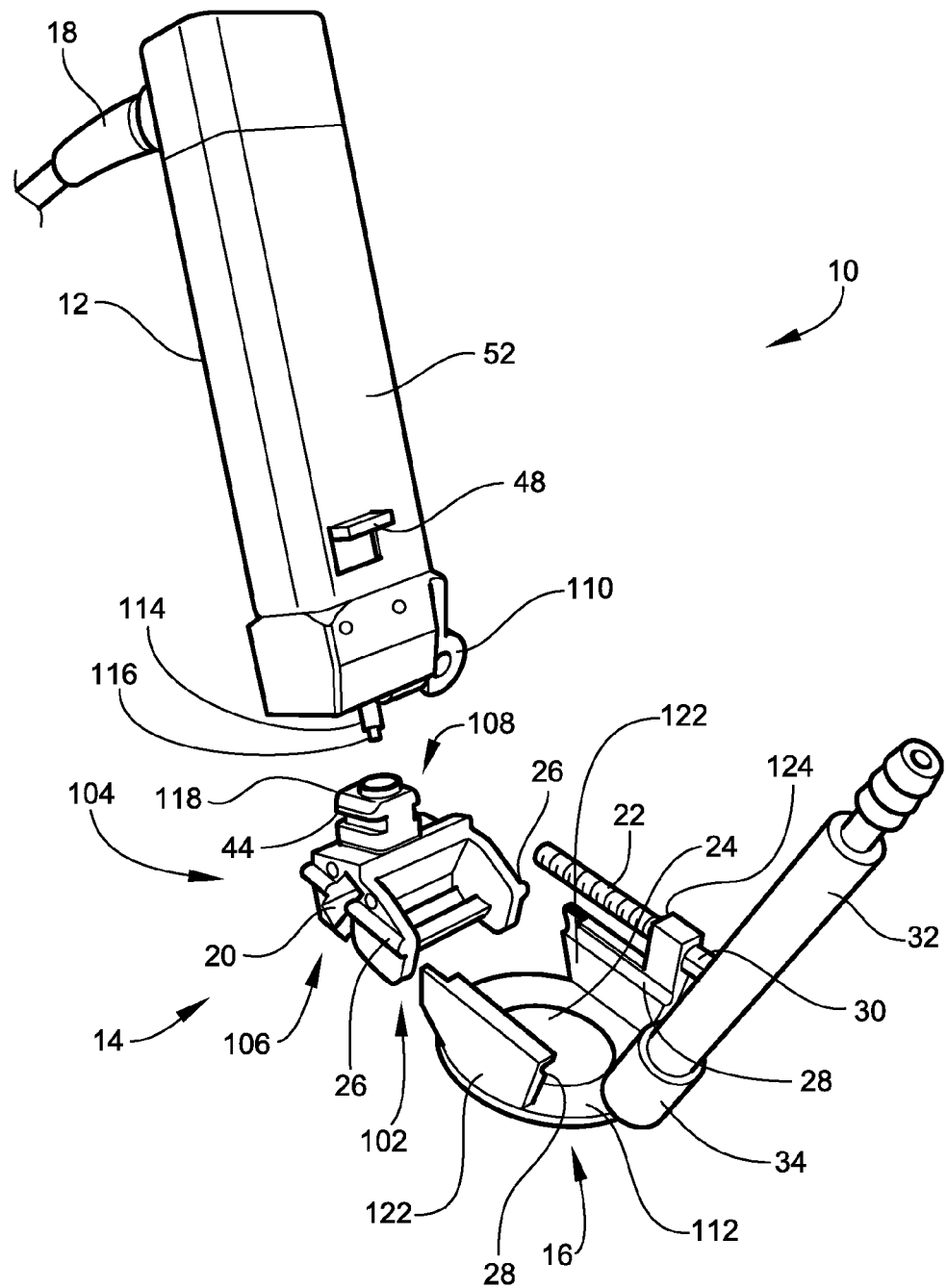
FIG. 1 is an exploded view of a microkeratome assembly of the present invention.
Figure 2:
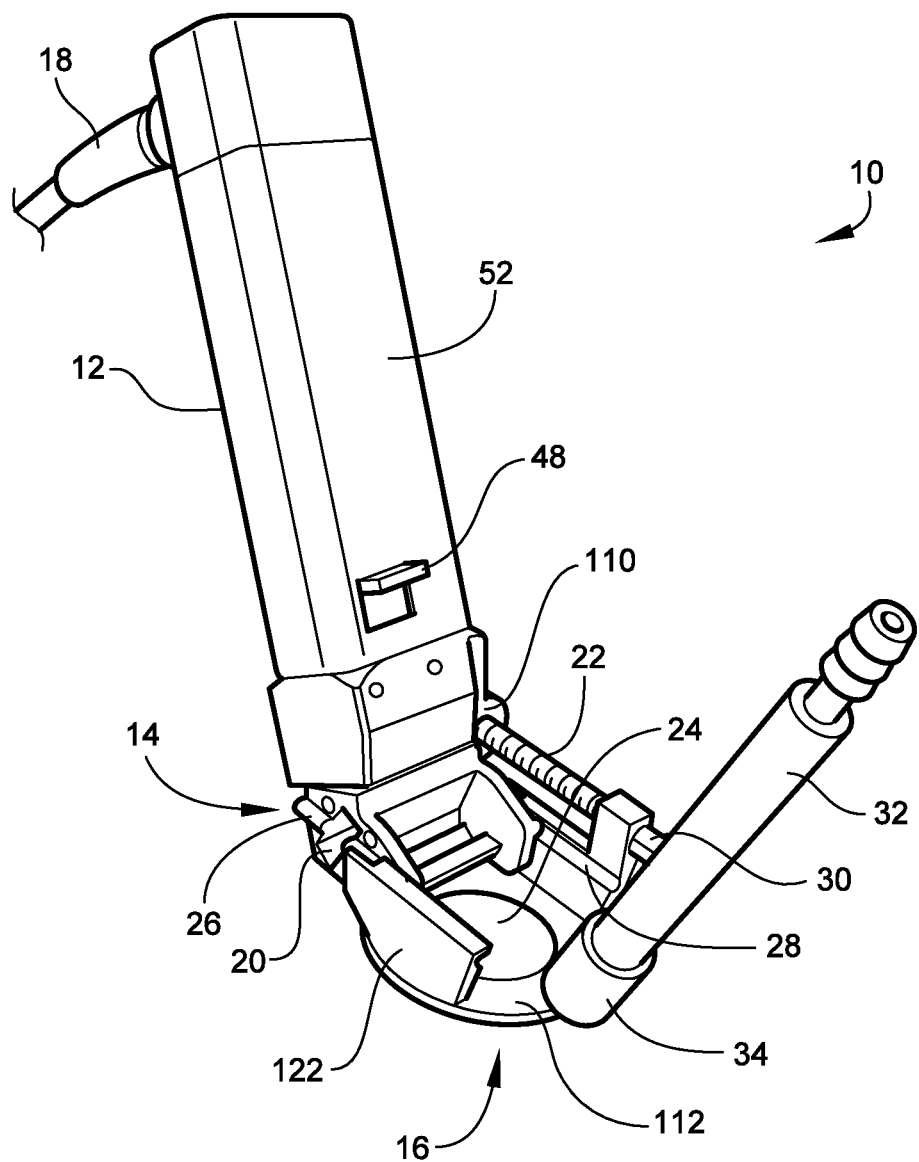
FIG. 2 is a perspective view of the microkeratome.

Referring to the drawings more particularly by reference numbers, FIGS. 1 and 2 show an embodiment of a microkeratome 10 of the present invention. The microkeratome 10 includes a hand piece 12 that is connected to a head 14 and a ring assembly 16. The microkeratome 10 is typically used to cut a lamella flap in a cornea (not shown) as part of a LASIK procedure. The ring assembly 16 may be attached to a source of vacuum to create a suction pressure between the ring 16 and the cornea. The suction pressure fixes the microkeratome 10 to the cornea. The hand piece 12 has a wire assembly 18 that is connected to an electrical console (not shown). The console provides electrical power to actuate the microkeratome 10.

The head 14 generally includes a front side 102, a rear side 104, a bottom side 106, and a top side 108. The head 14 has a blade cavity 20 that can receive a blade, or a blade and a blade holder to which the blade is mounted (not shown). The ring assembly 16 may include a helical gear 22 that is coupled to the hand piece 12. For example, the helical gear 22 may be coupled to an internal gear (not shown) of the hand piece 12 at a coupling location 110. The hand piece 12 includes a motor (not shown) that cooperates with the helical gear 22 to move the head 14 and blade in a linear direction across an opening 24 of the ring assembly 16. The opening 24 is formed through a top surface 112 of the ring assembly 16 that faces the bottom side 106 of the head 14 and its blade. The cornea may protrude through this opening 24.

To accurately guide the head 14 and the blade along the linear direction, the head 14 and ring assembly 16 may have one or more corresponding linear bearing members such as, for example, one or more corresponding tongues 26 and grooves 28, respectively, that create linear bearings. In the illustrated example, the tongues 26 are formed on the head 14 and the grooves 28 are formed on the ring assembly 16. Alternatively, the tongues 26 may be formed on the head 14 and the grooves 28 may be formed on the ring assembly 16. In another alternative, the head 14 may include a tongue 26 that movably engages a corresponding groove 28 of the ring assembly 16, and the head 14 may also include a groove 28 that is engaged by a corresponding tongue 26 of the ring assembly 16.

The hand piece 12 may contain another motor (not shown) that moves the blade in a lateral reciprocating (or oscillating) manner (i.e., orthogonal or transverse to the linear direction along which the head 14 moves) so that the blade cuts corneal tissue and creates a lamella flap. For example, this other motor may drive the rotation of a shaft 114 that includes an eccentric cam or pin 116. When the head 14 is attached to the hand piece 12 in this example, the shaft 114 extends through a coupling member 118 generally disposed at or near the top side 108 of the head 14 and the eccentric pin 116 engages a slot (not shown) of the blade (or blade holder). The coupling member 118 or some other portion of the structure of the head 14 may have a groove 44 utilized to attach the head 14 to, and detach the head 14 from, the hand piece 12 in a manner described below. The coupling member 118 of the head 14 may be oriented such that the hand piece 12 is oriented at a non-zero angle relative to the top surface 112 of the ring assembly 16.

The ring assembly 16 may include one or more side walls 122 that extend upward from the top surface 112 of the ring assembly 16 on either side of the opening 24 of the ring assembly 16. The linear bearing member(s) associated with the ring assembly 16 (e.g., tongues 26 and/or grooves 28 as described above) may be formed in the side wall(s) 122 as illustrated in the example of FIGS. 1 and 2. A bore 124 may be formed in one of the sidewalls 122 to receive the helical gear 22. The ring assembly 16 may further include a nut 30 that is attached to the helical gear 22. The nut 30 can be removed to allow the hand piece 12 and head 14 to be detached from the ring assembly 16. This allows the hand piece 12, head 14 and blade to be removed even while the ring 16 is applying suction to a cornea. By way of example, the microkeratome 10 may be actuated to initiate cutting of a cornea by the blade. A complication may occur which causes the surgeon to de-actuate the microkeratome 10 and stop the cutting process. Under suction the ring 16 flattens out the cornea. If the suction is removed the cornea may move back to its natural shape. This movement may cause undesirable movement between the blade and corneal tissue. The nut 30 allows the hand piece 12, head 14 and the blade to be removed from the cornea without removing the suction of the ring 16.

The ring assembly 16 may include an aspiration connector 32. The aspiration connector 32 is connected to an aspiration tube (not shown) and is coupled to aspiration openings (not shown) in the ring. The aspiration connector 32 may have a collar 34 that limits the travel of the head 14 and the blade. The aspiration connector 32 may have a threaded shaft (not shown) that screws into a corresponding threaded opening (not shown) of the ring assembly 16.

Figure 3:
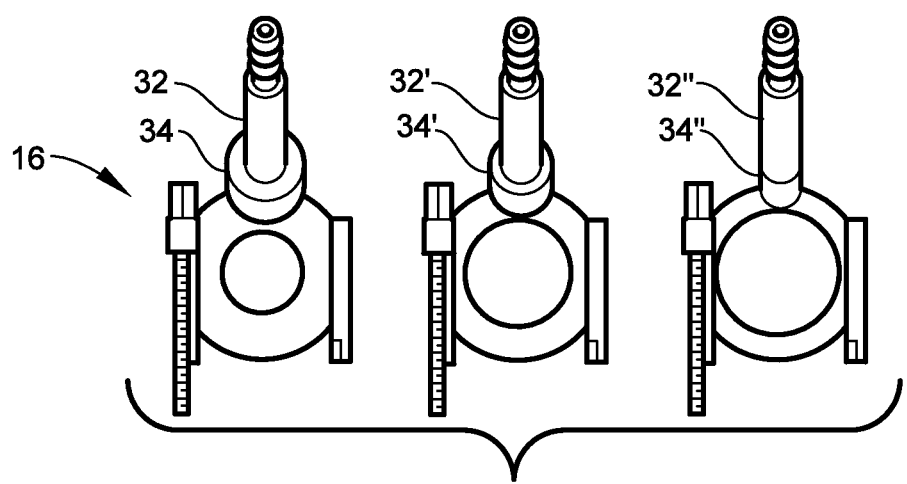
FIG. 3 is a top view showing three different aspiration connectors.

FIG. 3 shows a plurality of aspiration connectors 32, 32' and 32" that each have collars 34, 34' and 34". Each collar 34, 34' and 34" has a different diameter. The thickness of the lamella flap can be varied by attaching different connectors 32, 32' or 32" to the ring assembly 16. For example, connector 32 may create a relatively thin flap. Connector 32' may create a thicker flap and connector 32" may create an even thicker flap. The different connectors 32, 32' and 32" allow the surgeon to vary the thickness of a lamella hinge.

Alternatively, the helical gear 22 can provide a stop function. The stop function may be provided by the end of the threads near the fastener 30. The stop function could also be provided by a nut attached to the threads of the gear 22. The size of the flap hinge can be varied by changing gears 22.

Figure 4:
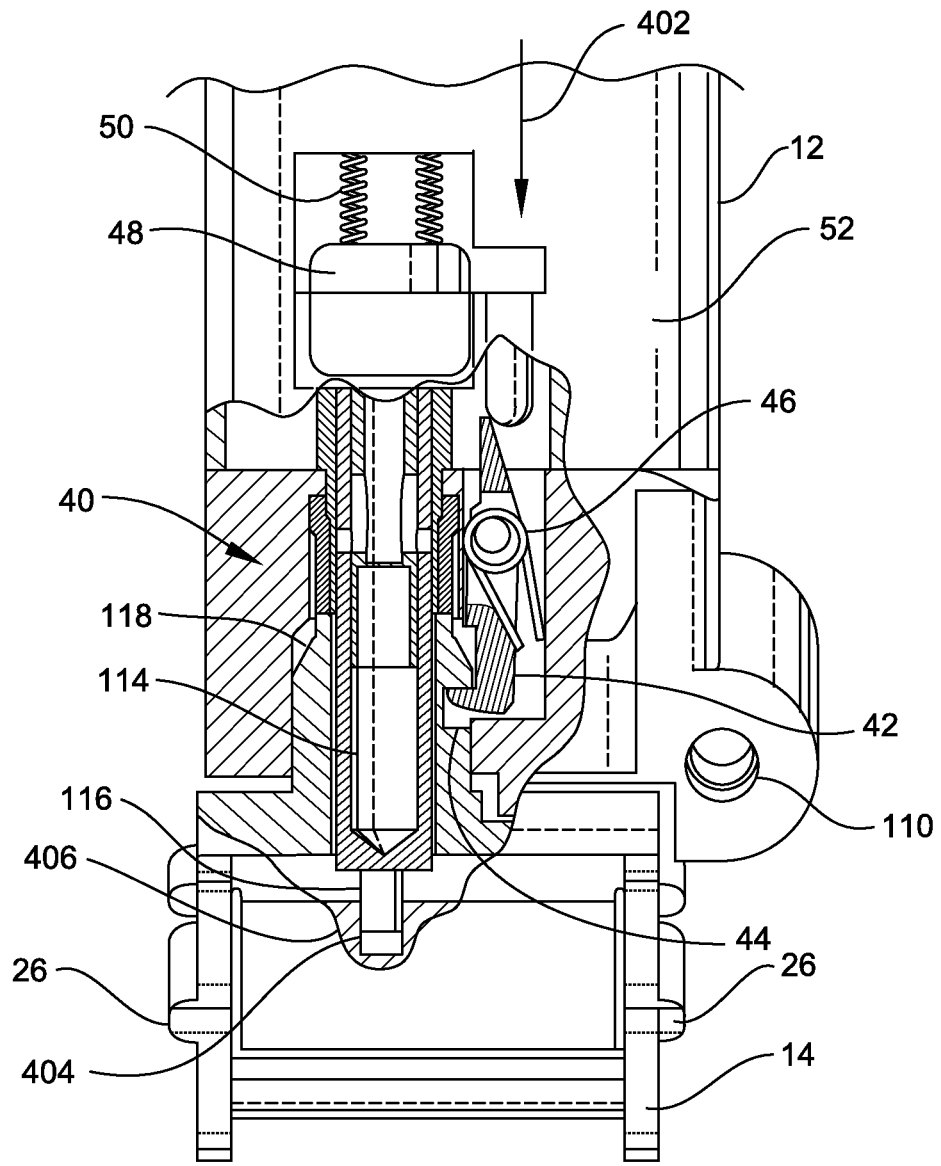
FIG. 4 is a sectional view showing a latch assembly of the microkeratome.

FIG. 4 shows a latch assembly 40 that connects the head 14 to the hand piece 12. The latch assembly 40 may include a latch 42 that is pivotally connected to the hand piece 12 and fits within the groove 44 of the head 14. In the illustrated example, the groove 44 is formed in the coupling member 118 of the head 14. The latch assembly 40 may include a return spring 46 that biases the latch 42 into the groove 44.

The latch assembly 40 may further have an actuator 48 that can be depressed by a user to move in a downward direction as indicated by an arrow 402 to rotate the latch 42 out of the groove 44. Alternatively, the actuator 48 may be configured to be actuated by the user in a lateral direction (i.e., transverse to the arrow 402 and the linear movement of the hand piece 12 and the head 14 relative to the ring assembly 16), which may assist in preventing accidental detachment of the head 14 from the hand piece 12 during a surgical procedure. The assembly 40 may include a return spring(s) 50 to move the actuator 48 back when released by the user. As shown in FIGS. 1, 2 and 4, the actuator 48 may be located on a first face 52 of the hand piece 12.

A user can attach the head 14 to the hand piece 12 by moving the head 14 until the latch 42 snaps into the groove 44. The head 14 can be removed from the hand piece 12 by depressing the actuator 48 to pull the latch 42 out of the groove 44. The head 14 may then be sterilized and re-attached to the hand piece 12. Alternatively, the head 14 may be replaced. By way of example, the head 14 may be constructed from a low cost plastic material that is replaced after every procedure. The hand piece 12 may also be constructed from a plastic material. The head 14 may be constructed from the same plastic material as the hand piece 12. By way of example, the plastic may be a polycarbonate or polysulphone.

FIG. 4 also illustrates the shaft 114 and the eccentric pin 116 of the motor that drives the lateral oscillatory motion of the blade (or blade holder). The shaft 114 may extend through the bore of the coupling member 118 of the head 14. The eccentric pin 116 engages a slot 404 of the blade (or blade holder) 406.

Figure 5:
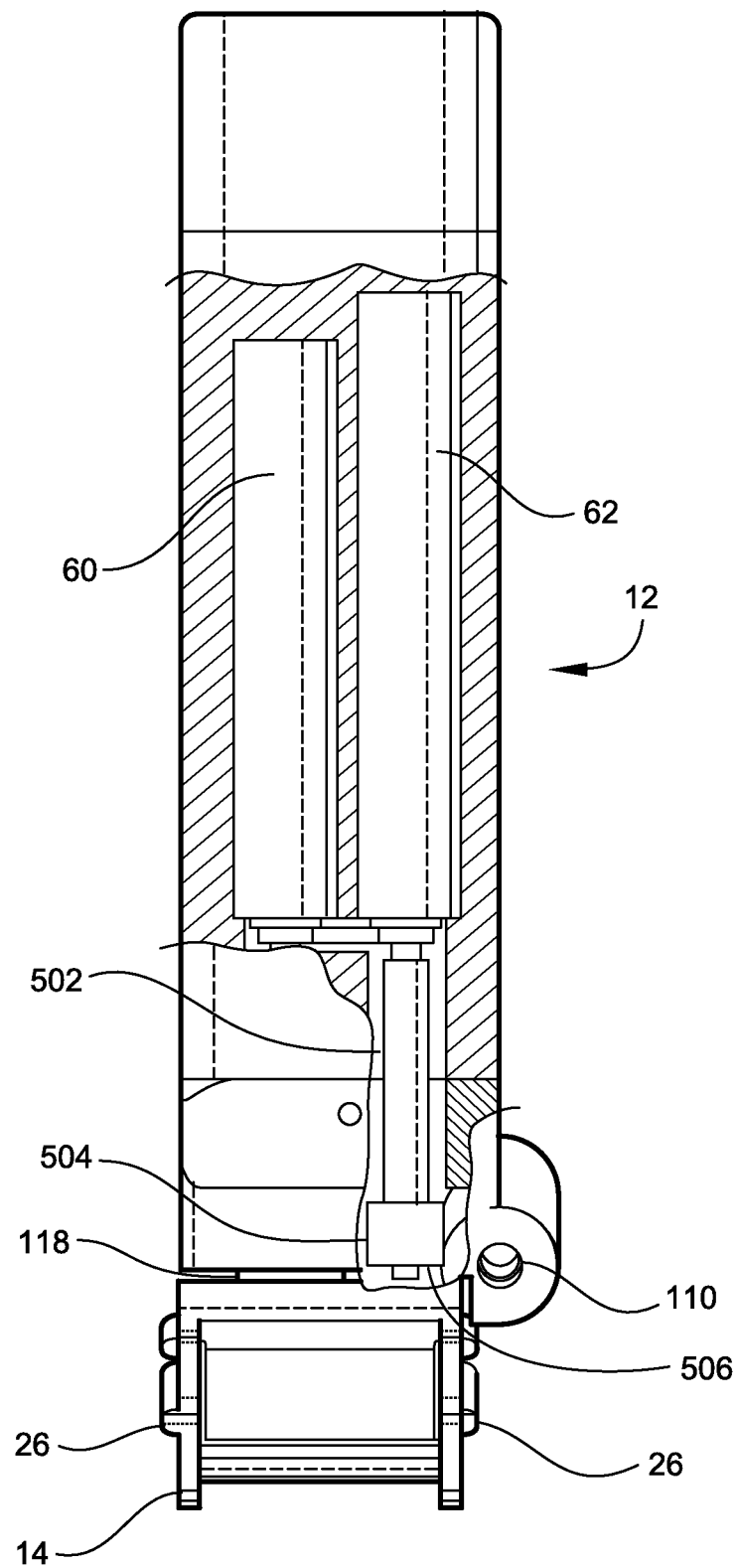
FIG. 5 is a sectional view showing motors of the microkeratome.

FIG. 5 shows a pair of motor assemblies 60 and 62 within the hand piece 12. Motor assembly 60 may move the blade in a lateral reciprocating manner. Motor assembly 62 may be coupled to the elongated helical gear 22 of the ring assembly 16 to pull the head 14 and blade across the ring opening 24. In the present context, the term "assembly" indicates one or more components (e.g., motor, shaft, linkage, gear, etc.) as needed to effect the movement of the blade in the linear and lateral directions via a source of power disposed in or coupled to the hand piece 12. In the illustrated example, the motor assembly 62 that drives the linear motion of the head 14 and blade may include a shaft 502 and one or more internal gears 504 and 506. In this example, the internal gear 506 includes threads in mating engagement with the threads of the helical gear 22. The internal gear 506 may, for example, have an annular structure in which internal threads engage the helical gear 22 and external threads engage another internal gear 504 (or directly to threads provided on the shaft 502). In this example, the helical gear 22 does not itself rotate. Consequently, the internal gear 506 functions as a rotating, linearly moving worm gear that is driven by the motor assembly 62 to travel along the length of the helical gear 22. By way of the mating engagement between the moving internal gear 506 and the stationary helical gear 22, the hand piece 12, head 14 and blade are pulled forward in the linear direction along which the helical gear 22 is oriented.

Figure 6:
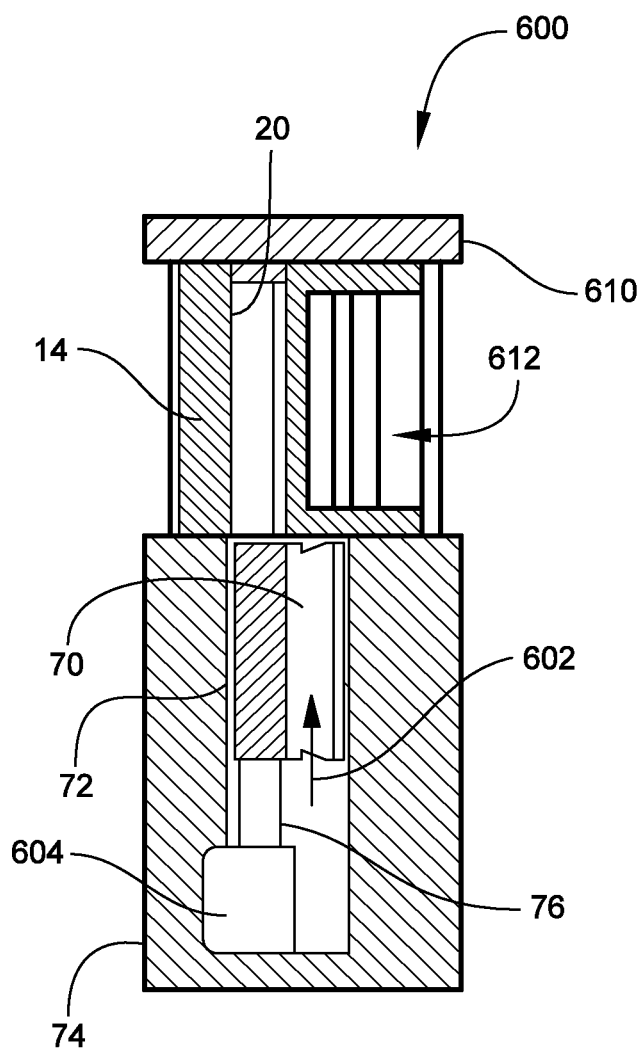
FIG. 6 is a top sectional view showing a blade being loaded into a head of the microkeratome from a blade shuttle.

As shown in FIG. 6, a blade (or a blade mounted to a blade holder) 70 may be packaged within a blade shuttle 600. The blade shuttle 600 may include a housing 74 having a housing interior 72 that holds the blade 70. In advantageous implementations, the housing 74 encloses the blade 70 in a sealed, sterile condition prior to use of the blade 70. The blade shuttle 600 may further include a plunger 76 located in the housing 74. The plunger 76 may be operated to push the blade 70 into the head 14 along a blade-loading direction 602. For this purpose, a portion 604 of the plunger 76 (e.g., a tap, button, finger grip, or the like) may be accessible from outside the housing 74 for manipulation by the user. The blade shuttle 600 may further include a drawer 610 that slides out from the housing 74 to the open position illustrated in FIG. 6. The drawer 610 has a drawer opening 612 communicating with the housing interior 72. The drawer opening 612 receives the head 14 in preparation for operating the plunger 76 to push the blade 70 into the blade cavity 20 of the head 14.

The blade shuttle 600 may have an alignment pin (not shown) that is inserted into a corresponding alignment hole (not shown) of the head 14 to align the blade 70 with the head cavity 20. The housing 74 may include a stop (not shown) that limits the travel of the plunger 76 and the location of the blade 70 within the head 14. The stop provides a feature that allows for the blade 70 to be accurately located within the head cavity 20 in a repeatable manner. It is desirable to accurately locate the blade 70 within the blade cavity 20 so that the eccentric pin 116 (FIG. 4) of the motor assembly 60 (FIG. 5) is properly coupled to the corresponding slot 404 (FIG. 4) of the blade 70.

In use, the blade shuttle 600 may be initially provided to the user as a package that contains the blade (or blade holder) 70 in a sterile condition within the housing interior 72. To install the blade 70 into the head 14, the user may slide out the drawer 610 to reveal the drawer opening 612, position the head 14 in the drawer opening 612 such that the blade cavity 20 is in proper alignment with the blade 70, and operate the plunger 76 (such as by manipulating the exposed portion 604) to transfer the blade 70 from the housing 74 into the blade cavity 20. The blade shuttle 600 may be discarded thereafter.

Figure 7:
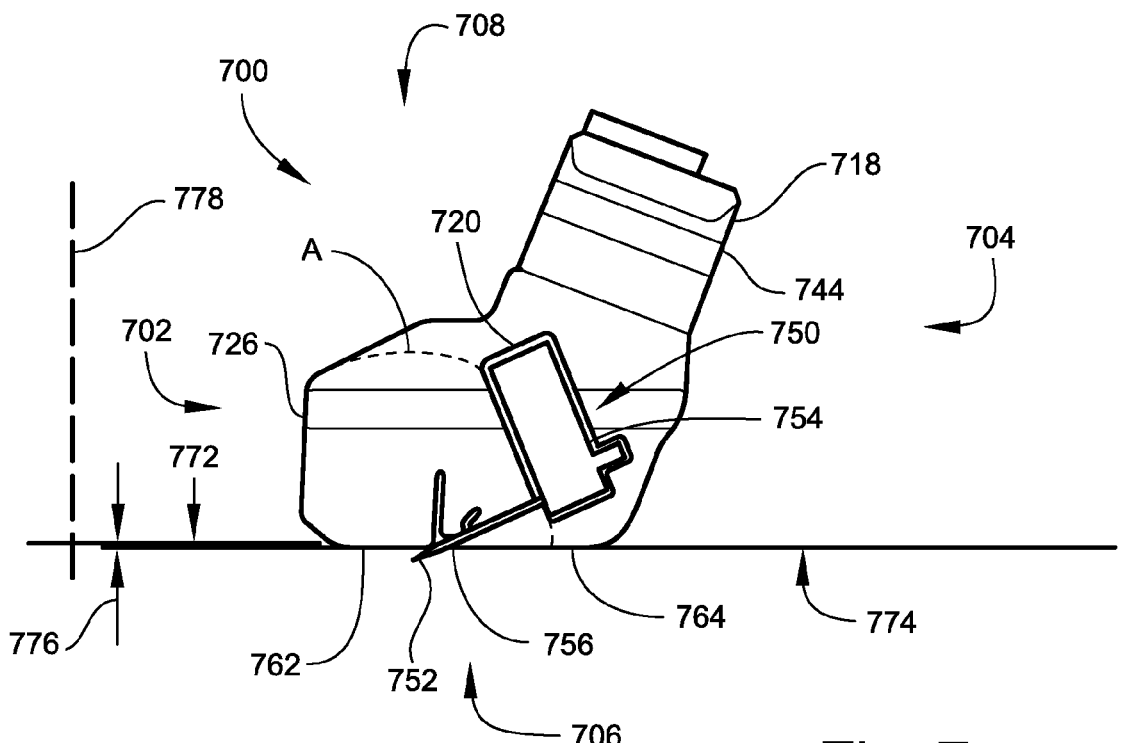
FIG. 7 is a side elevation view of a microkeratome cutting head according to another implementation.

FIG. 7 is a side elevation view of a microkeratome cutting head 700 according to another implementation. The cutting head 700 may share many of the same or similar features as those illustrated in FIGS. 1, 2, 4 and 5, and accordingly such features are designated by similar reference numerals in FIG. 7. In FIG. 7, a blade assembly 750 including a blade 752 mounted to a blade holder 754 is shown installed in the blade cavity 720 of the cutting head 700 for use during a surgical procedure. A blade opening 756 formed at the bottom side 706 of the cutting head 700 communicates with the blade cavity 720. At the installed position of the blade assembly 750, at least a portion of the blade 752 that includes its cutting edge extends out from the bottom side 706 of the cutting head 700. The cutting head 700 includes an applanation plate 762 and a stromal plate 764, which are generally located at the bottom side 706 of the cutting head 700. The applanation plate 762 is located in front of the blade opening 756 and the stromal plate 764 is located behind the blade opening 756. The applanation plate 762 and the stromal plate 764 may be formed as an integral part of the main structure of the cutting head 700, or alternatively may be physically separate components attached to the structure of the cutting head 700 by any suitable means.

In use during a procedure for creating a corneal flap, the cutting head 700 is driven in the linear direction to the left from the perspective of FIG. 7, and is guided by the ring assembly as described above. As the cutting head 700 moves forward, the cornea first encounters the applanation plate 762, and then the blade 752, and then the stromal plate 764. As the applanation plate 762 comes into contact with the cornea, the applanation plate 762 flattens the cornea and creates intraocular pressure. The applanation plate 762 maintains these flattening and pressurized conditions as it passes over the cornea. While the cornea is flattened, the blade 752 begins to cut a corneal flap, which action is enhanced by driving the blade 752 into oscillatory motion along a lateral axis (i.e., into and out from the drawing sheet of FIG. 7) as described above. With continued forward movement of the cutting head 700, the stromal plate 764 passes over the region of the stroma (or stromal bed) that has been exposed as a result of the cutting.

As noted above, a problem attending the use of microkeratome cutting heads of known designs is the occurrence of a buttonhole (or dimple) in the cornea, which is a result of the cutting procedure. A buttonhole generally is a depression in the central region of the cornea, which results in an uncut island of tissue and is created as a conventionally designed cutting head passes over the cornea. The buttonhole is highly undesirable as it results in the blade cutting only the peripheral tissue that is at a higher elevation than the tissue in the central cornea where the buttonhole exists. Thus, a flap having a hole at its center is thereby created instead of an intended continuous or unbroken corneal flap. The cutting head 700 illustrated in FIG. 7 prevents the occurrence of a buttonhole and attendant complications, as will now be described.

We have now discovered that a major cause for the occurrence of buttonholes relates to the respective elevations of the applanation plate and the stromal plate of a cutting head. In cutting heads of known designs, the applanation plate is typically disposed at the same elevation as the stromal plate or at a lower elevation than the stromal plate. While not wishing to be bound by any particular theory, we have determined that the higher the stromal plate is in relation to the applanation plate, the more likely a buttonhole may occur. We have found that the stromal plate, if properly located, can serve to maintain an intraocular pressure of sufficient magnitude and constancy that prevents the cornea from losing its firmness. These findings, the effect of the relative elevations or heights of the applanation plate and the stromal plate, and the role of the stromal plate have not been appreciated by persons skilled in the art prior to the present teachings.

The cutting head 700 illustrated in FIG. 7 addresses this problem by setting the elevation of the stromal plate 764 to be lower than the elevation of the applanation plate 762. Conceptually, the outward-facing surface of the applanation plate 762 lies in an applanation plate plane 772 and the outward-facing surface of the stromal plate 764 lies in a stromal plate plane 774. According to this implementation, the applanation plate plane 772 and the stromal plate plane 774 are not coplanar. Stated in another way, the applanation plate 762 and the stromal plate 764 lie in different planes 772 and 774, and the stromal plate plane 774 is lower than the applanation plate plane 772 by an elevation difference designated as 776 in FIG. 7.

From the perspective of FIG. 7, the elevations may be measured or defined along a vertical direction or axis 778, although it will be understood that no limitation is placed on the orientation of the cutting head 700 relative to any particular direction or plane of reference. In FIG. 7, the vertical direction 778 may be considered as being orthogonal to the applanation plate plane 772 or the stromal plate plane 774 and runs generally from the bottom side 706 to the top side 708 of the cutting head 700. It will be noted here that the applanation plate plane 772 and the stromal plate plane 774 may be generally or substantially parallel to each other. Here, the terms "generally" and "substantially" take into account some degree of imperfection or impreciseness in the process for fabricating the applanation plate 762 and the stromal plate 764. The elevation difference 776 between the applanation plate 762 and the stromal plate 764 may be measured along the vertical direction 778. When considering the individual heights or elevations of the applanation plate 762 and the stromal plate 764, any reference point, line or plane may be utilized. For instance, the elevation of the stromal plate 764 may be taken to be zero and the higher elevation of the applanation plate 762 then considered relative to such zero datum. As other examples, the respective elevations of the applanation plate 762 and the stromal plate 764 may be considered relative to some other surface of, or point on, the cutting head 700, a surface of or point on the ring assembly 16 (FIG. 1), a point on the cornea, etc.

As a result of the configuration illustrated in FIG. 7, in operation as the applanation plate 762 passes over the pressurized cornea and the blade 752 begins to cut the corneal tissue, the lower-elevation stromal plate 764 in effect replaces the corneal tissue that has just been removed by the blade 752. This enables the intraocular pressure to be maintained and prevents the occurrence of a buttonhole. It will be noted that the cutting head 700 is configured to create a corneal flap of a specified thickness. In some implementations, the thickness ranges from 10 µm to 150 µm. As one specific example, the thickness may be 100 µm. In another specific example, the thickness may be 130 µm. We have discovered the setting of the elevation difference 776 between the applanation plate 762 and the stromal plate 764 in proportion to the flap thickness to be an effective implementation. In particular, the elevation difference 776 may be set to be approximately or substantially equal to the flap thickness. Here, terms such as "approximately" or "substantially" encompass a deviation of ±5 µm as between the elevation difference 776 and the flap thickness. Thus, for example, in a case where the cutting head 700 is configured for creating a corneal flap of 100 µm thickness, the stromal plate 764 is set to be 100 µm (or 100±5 µm) lower than the applanation plate 762.

Figure 8:
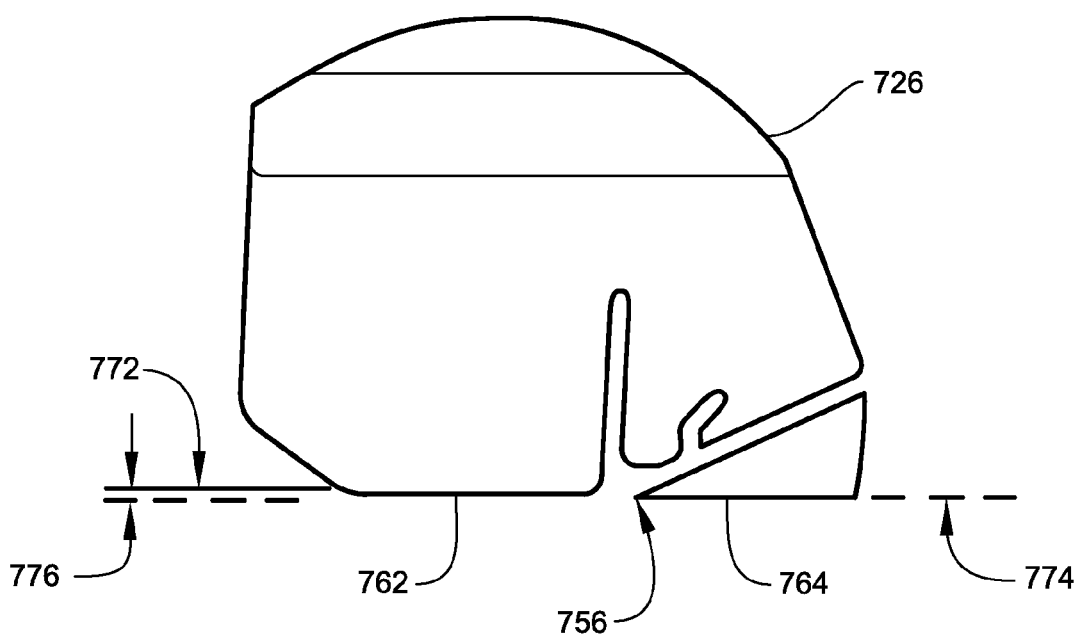
FIG. 8 is a detailed view of the region designated "A" in FIG. 7.

FIG. 8 is a detailed view of the region designated "A" in FIG. 7, from which the respective heights of the applanation plate 762 and the stromal plate 764 may be better visualized.

The cutting head 700 may be attachable to/detachable from the hand piece 12 and the ring assembly 16, and may be driven by one or more motor assemblies 60 and 62, in accordance with the implementations described above and illustrated in FIGS. 1-5. Moreover, the blade shuttle 600 described above and illustrated in FIG. 6 may be utilized to load the blade 752 or blade assembly 750 into the blade cavity 720 of the cutting head 700 illustrated in FIGS. 7 and 8.

Figure 9:
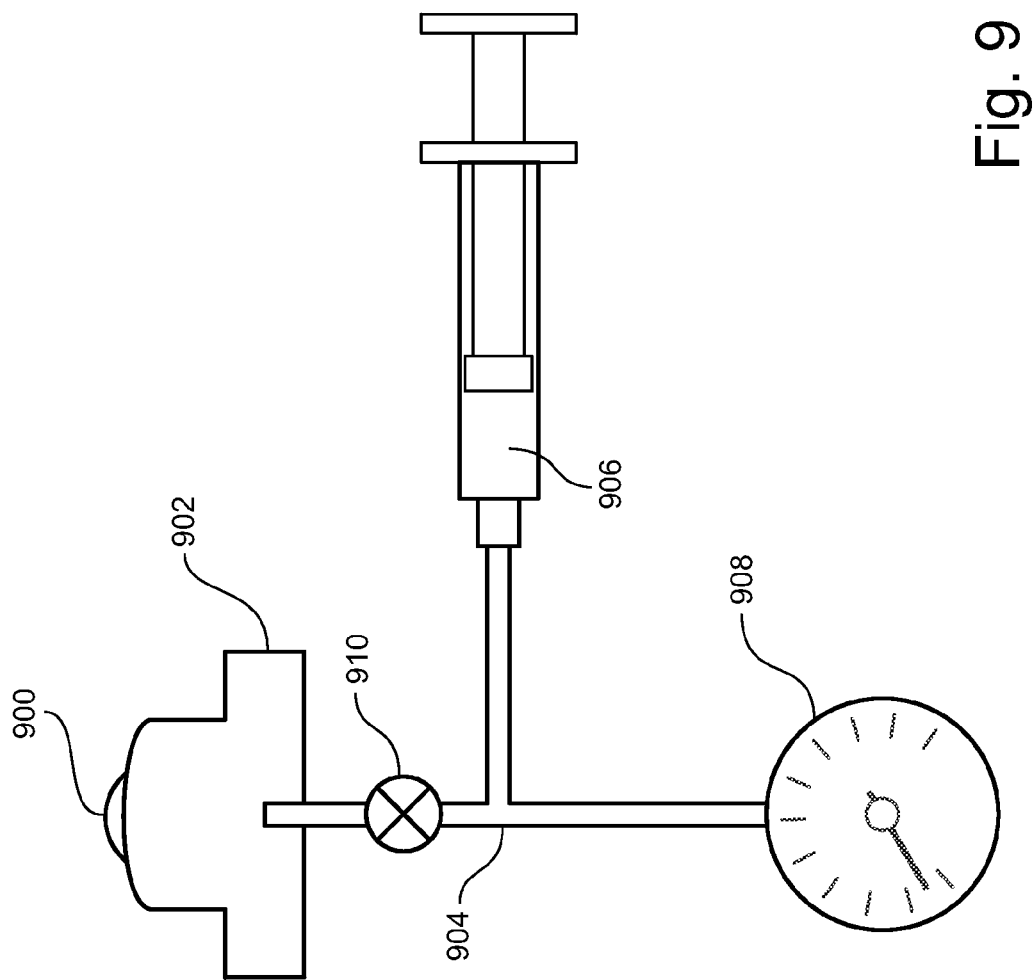
FIG. 9 is a schematic view of a preferred embodiment artificial anterior chamber system.

The above-described microkeratome system may be used in conjunction with an artificial anterior chamber (AAC) 902 shown in FIG. 9. The microkeratome procedure is applied to a donor eye 900 that is held inside the artificial anterior chamber 902.

Figure 10:
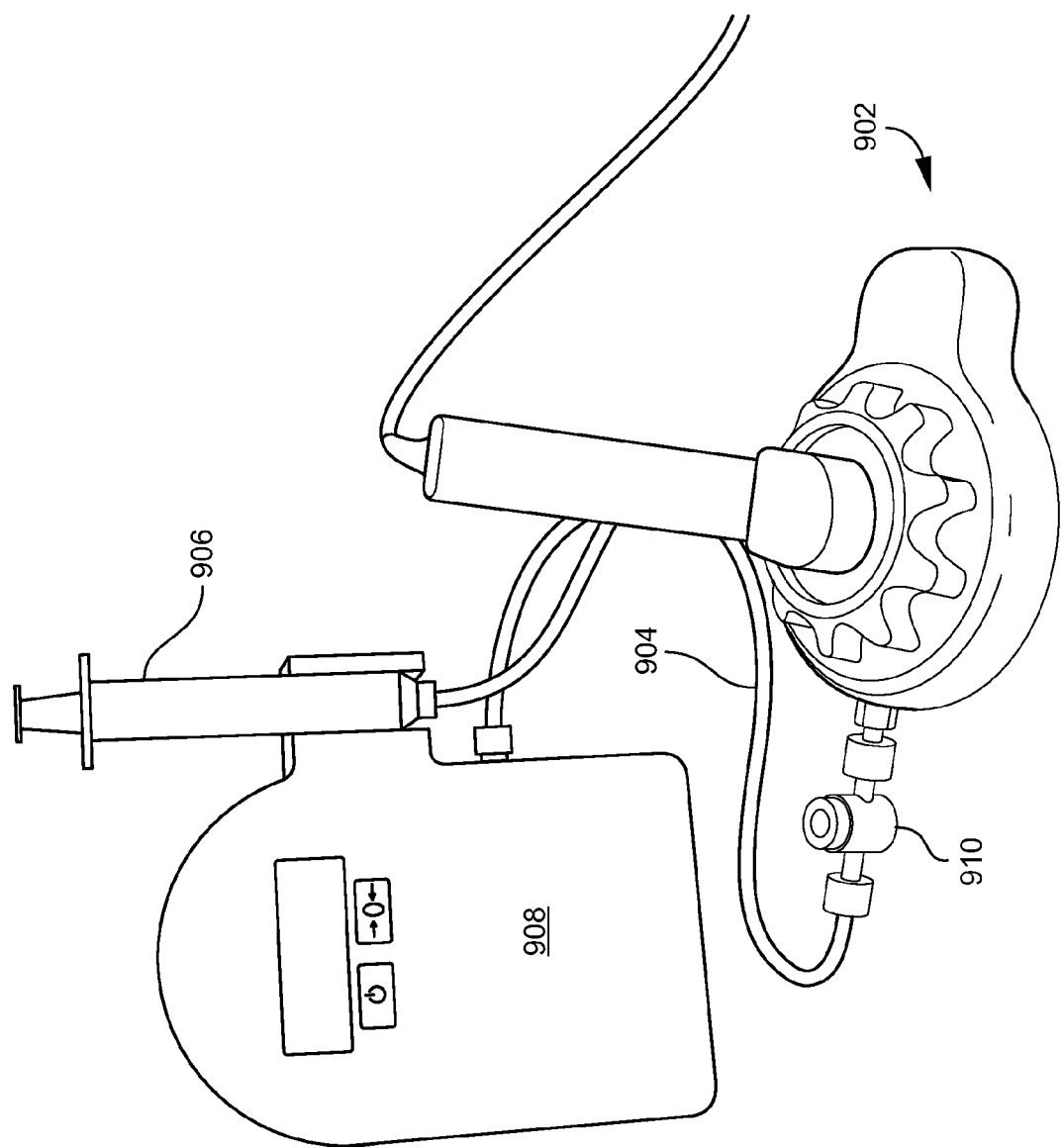
FIG. 10 shows a preferred embodiment artificial anterior chamber system with an artificial anterior chamber connected via tubing with a syringe pressure source connected via tubing with a pressure monitoring gauge and a microkeratome attached to the artificial anterior chamber.
Figure 11:
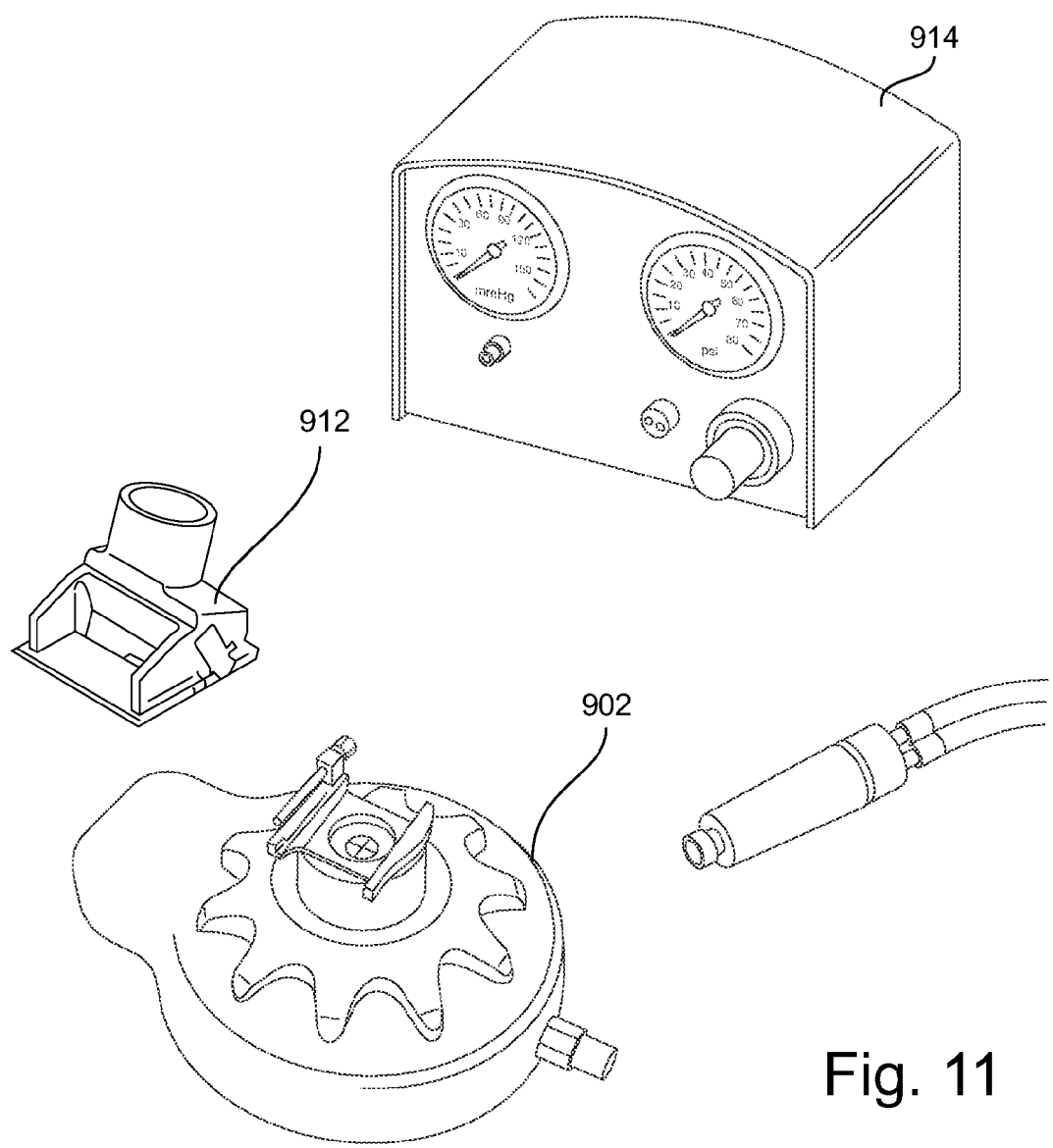
FIG. 11 shows an alternative embodiment artificial anterior chamber system having an artificial anterior chamber, a one-piece cutting head of from a microkeratome, and a console having pressure gauges and a knob controlling a valve to adjust line pressure.

The system depicted in FIG. 9 can be implemented with a pressure gauge in a standalone arrangement as seen in FIG. 10, or in an alternative embodiment, implemented with a pressure gauge built into a console as seen in FIG. 11.

FIG. 10 shows a preferred embodiment artificial anterior chamber system with an artificial anterior chamber 902 connected via tubing with a syringe pressure source 906 connected via tubing with a pressure monitoring gauge 908. The pressure gauge 908 has a digital display indicating line pressure, which is the pressure being exerted on the donor eye inside the AAC. A microkeratome with its handle extending straight upward is attached to the top of the artificial anterior chamber 902. FIG. 10 further shows the pressure gauge 908 and the AAC 902 situated on a flat surface (e.g., work table) so the two are preferably at the same level or height off the ground. This ensures a constant pressure head from fluid mechanics principles, thus producing accurate readings for the pressure gauge 908 and precisely controlled pressures exerted on the donor eye during the procedure.

FIG. 11 shows an alternative embodiment artificial anterior chamber system having an artificial anterior chamber 902, a one-piece cutting head 912 from a microkeratome, and a console 914 having pressure gauges and an optional knob controlling a valve inside the console to adjust system/line pressure. The pressure gauges provide pressure in dual analog dial displays in psi and mmHg.

FIGS. 9 and 10 disclose a preferred embodiment system for preparing stromal/endothelial cell tissue from a donor eye using a microkeratome in conjunction with an artificial anterior chamber (AAC) device 902. The AAC device 902 is made from a housing, wherein a chamber within the housing configured for receiving a donor eye 900 and maintaining the donor eye at an applied pressure. There is an opening communicating with the chamber, the opening configured for exposing a corneal section of the donor eye 900 and mounting the microkeratome in a position at which the microkeratome can interface with the donor eye. There are a first fluid connector communicating with the chamber in a closed loop system; a fluid pressure source (e.g., syringe, pump, bag, plenum, or the like) 906 having a second fluid connector; a first fluid conduit connected between the AAC device 902 and the fluid pressure source 906 at the first fluid connector and the second fluid connector, respectively, and having a third connector (e.g., a T-junction connector) 904 located along a length of the first fluid conduit; a second fluid conduit connected to the third fluid connector; and a pressure monitoring gauge 908 of the closed loop system having a fourth fluid connector connected to the second fluid conduit, and a display 908 configured for displaying an indication of the pressure applied by the fluid pressure source 906 to the chamber.

As seen in FIGS. 9-11, the present invention further contemplates a preferred method for preparing stromal/endothelial cell tissue of a donor eye for endothelial keroplasty using a microkeratome having a cutting head 912, the method including the steps of mounting the donor eye 900 in a chamber of an artificial anterior chamber (AAC) device 902 such that a corneal section of the donor eye is exposed via an opening of the AAC device; mounting the microkeratome in the opening such that the corneal section is accessible by the cutting head 912 of the microkeratome; placing a fluid pressure source 906 in communication with the chamber in a closed loop system by interconnecting a first fluid conduit between the fluid pressure source and the chamber; placing a pressure monitoring gauge 908, 914 in communication with the chamber by interconnecting a second fluid conduit between the pressure monitoring gauge and the first fluid conduit, at a location of the first fluid conduit between the fluid pressure source and the AAC device; applying pressure to the donor eye by operating a fluid pressure source 906, 914 communicating with the chamber via a first fluid conduit; cutting stromal/endothelial cell tissue from the donor eye by operating the microkeratome; while cutting, monitoring the pressure applied to the donor eye by operating the pressure monitoring gauge 908, 914 in the closed loop system, wherein the pressure monitoring gauge displays an indication of the pressure being applied; and based on the pressure indication displayed, adjusting the fluid pressure source 906, 914 and/or via valve 910 to maintain the applied pressure within a range of about 75 to 125 mmHg.

As depicted in FIG. 9, in a preferred method, the present invention further contemplates using a split tubing 904 carrying the medium (preferably, balanced salt solution or air) that allows the pressure source 906 to be monitored by a gauge 908 (preferably in range of about at least 20 mmHg to 300 mmHg of pressure) that will help prevent excessive pressure that damages the endothelial cells located on the inner lining of the donor cornea that is positioned in the artificial anterior chamber 902. Via empirical observations, the applied pressure is more preferably within a range of about 75 to 125 mmHg. Further, empirical observations in the field reveal that many eye bank workers unknowingly apply pressure to the donor cornea in excess of 200 mmHg, which kills many of the endothelial cells the workers are actually trying to save and implant into a human recipient. Indeed, empirical observations have shown that glaucoma patients can lose endothelial cells when they experience elevated pressure of 30 mmHg.

The preferred embodiment of the present invention is based on a closed loop system, shown in FIGS. 9 and 10, having no outflow or any leaks in the system while the cornea is being accurately cut by a microkeratome. In order to cut the cornea at an accurate thickness, the pressure of the donor cornea must be at a predictable pressure and that pressure must be maintained throughout the cutting process. A closed system is very important in this process. Therefore, in the preferred embodiment, the present invention system has a valve 910 situated between the donor cornea 900 in the artificial anterior chamber 902 and the split/T-junction connector 904 in the pressure line. The surgeon or user can close this valve 910 after the proper pressure is achieved. As the microkeratome passes over the donor cornea, the pressure in the donor cornea becomes elevated, which is predictable if the valve 910 is closed. Without this valve 910 and its proximate location adjacent to the AAC 902 to precisely control the line pressure, the increased pressure during the microkeratome pass becomes unpredictable, and could damage the donor eye and/or create an inaccurate tissue section.

It is understood that various aspects or details of the invention may be changed without departing from the scope of the invention. Furthermore, the foregoing description is for the purpose of illustration only and not for the purpose of limitation insofar as the invention is defined by the following claims.

What is claimed is:

1. A method for preparing stromal/endothelial cell tissue of a donor eye for endothelial keroplasty using a microkeratome, the method comprising:
   mounting a corneal section of the donor eye in a chamber of an artificial anterior chamber (AAC) device such that the corneal section is exposed via an opening of the AAC device;
   mounting a microkeratome in the opening such that the corneal section is accessible by a cutting head of the microkeratome;

placing a fluid pressure source in communication with the chamber in a closed loop system by interconnecting a first fluid conduit between the fluid pressure source and the chamber;

placing a pressure monitoring gauge in communication with the chamber by interconnecting a second fluid conduit between the pressure monitoring gauge and the first fluid conduit, at a location of the first fluid conduit between the fluid pressure source and the AAC device;

applying pressure to the corneal section by operating the fluid pressure source communicating with the chamber via the first fluid conduit;

cutting stromal/endothelial cell tissue from the corneal section by operating the microkeratome;

while cutting, monitoring the pressure applied to the corneal section by operating the pressure monitoring gauge in the closed loop system, wherein the pressure monitoring gauge displays an indication of the pressure being applied; and based on the pressure indication displayed, adjusting the fluid pressure source to maintain the applied pressure within the AAC device within a range of about 75 to 125 mmHg.

2. The method of claim 1, wherein at least one of the first and second fluid conduits includes a valve, and wherein the method includes controlling the pressure via the valve by locking the valve so that the pressure is at a specific level, and operating the valve to relieve an amount of increased pressure at the corneal section as the microkeratome cutting head interfaces the corneal section.

3. The method of claim 1, wherein the method includes locating the pressure gauge at about the same level as the artificial anterior chamber in order to minimize an inaccurate pressure value.

4. The method of claim 2, wherein the method includes locating the valve at the first fluid conduit immediately adjacent the AAC device.

* * * * *